US010881710B2

(12) United States Patent
Bar-Or

(10) Patent No.: US 10,881,710 B2
(45) Date of Patent: Jan. 5, 2021

(54) TREATMENT OF RHINITIS

(71) Applicant: AMPIO PHARMACEUTICALS, INC., Greenwood Village, CO (US)

(72) Inventor: David Bar-Or, Englewood, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

(21) Appl. No.: 14/353,833

(22) PCT Filed: Oct. 26, 2012

(86) PCT No.: PCT/US2012/062152
§ 371 (c)(1),
(2) Date: Apr. 24, 2014

(87) PCT Pub. No.: WO2013/063413
PCT Pub. Date: May 2, 2013

(65) Prior Publication Data
US 2014/0294738 A1 Oct. 2, 2014

Related U.S. Application Data

(60) Provisional application No. 61/552,508, filed on Oct. 28, 2011, provisional application No. 61/561,215, filed on Nov. 17, 2011.

(51) Int. Cl.
| *A61K 38/12* | (2006.01) |
| *A61K 45/06* | (2006.01) |
| *A61K 31/495* | (2006.01) |
| *A61K 38/38* | (2006.01) |
| *A61M 11/02* | (2006.01) |
| *A61M 15/00* | (2006.01) |
| *A61K 9/00* | (2006.01) |
| *A61M 15/08* | (2006.01) |

(52) U.S. Cl.
CPC ............ *A61K 38/12* (2013.01); *A61K 31/495* (2013.01); *A61K 38/385* (2013.01); *A61K 45/06* (2013.01); *A61M 11/02* (2013.01); *A61M 15/009* (2013.01); *A61M 15/0065* (2013.01); *A61K 9/0043* (2013.01); *A61M 15/08* (2013.01); *A61M 2202/064* (2013.01)

(58) Field of Classification Search
None
See application file for complete search history.

(56) References Cited

U.S. PATENT DOCUMENTS

| 3,763,091 A | 10/1973 | Crescenzi et al. |
| 3,772,265 A | 11/1973 | Isowa et al. |
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A * | 7/1990 | Shimazaki ........... C07D 241/08 514/252.13 |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,358,953 A * | 10/1994 | Alker ................... C07D 471/04 514/290 |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,561,115 A | 10/1996 | Tenold |
| 5,578,323 A | 11/1996 | Milstein et al. |
| 5,589,501 A | 12/1996 | Carrera et al. |
| 5,648,486 A | 7/1997 | Cai et al. |
| 5,665,714 A | 9/1997 | Paltauf et al. |
| 5,693,338 A | 12/1997 | Milstein |
| 5,700,804 A | 12/1997 | Collins et al. |
| 5,703,093 A | 12/1997 | Cai et al. |

(Continued)

FOREIGN PATENT DOCUMENTS

| CN | 1120439 | 4/1996 |
| CS | 254868 | 6/1987 |

(Continued)

OTHER PUBLICATIONS

Meltzer et al., Efficacy and Patient Satisfaction with Cromolyn Sodium Nasal Solution in the Treatment of Seasonal Allergic Rhinitis: A Placebo-Controlled Study, Clinical Therapeutics, vol. 24, No. 6, 2002 p. 942-952.*

(Continued)

*Primary Examiner* — Jennifer A Berrios
(74) *Attorney, Agent, or Firm* — Sheridan Ross P.C.

(57) ABSTRACT

The invention provides a method of treating rhinitis. The method comprises administering an effective amount of a pharmaceutical composition comprising a diketopiperazine with amino acid side chains of aspartic acid and alanine (DA-DKP) formulated for nasal administration. The invention also provides a pharmaceutical product comprising a DA-DKP containing composition.

10 Claims, No Drawings

(56) References Cited

U.S. PATENT DOCUMENTS

| | | |
|---|---|---|
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,811,241 A | 9/1998 | Goodfellow et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 1/2012 | Bar-Or et al. |
| 8,198,407 B1 | 6/2012 | Burton et al. |
| 8,217,047 B2 | 7/2012 | Bar-Or |
| 8,268,830 B2 | 9/2012 | Bar-Or et al. |
| 8,314,106 B2 | 11/2012 | Kraft |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 8,513,196 B2 | 8/2013 | Bar-Or et al. |
| 8,551,953 B2 | 10/2013 | Bar-Or et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goddey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0048795 A1* | 3/2004 | Ivanova ............. A61K 31/00 424/85.1 |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2009/0038416 A1* | 2/2009 | Bonner ............. B01L 3/5082 73/864.51 |
| 2010/0042206 A1 | 2/2010 | Yadav et al. |
| 2010/0120056 A1 | 5/2010 | Bar-Or |
| 2010/0190696 A1 | 7/2010 | Bar-Or et al. |
| 2010/0144611 A1 | 10/2010 | Bar-Or |
| 2012/0022081 A1 | 1/2012 | Bar-Or et al. |
| 2012/0058934 A1 | 3/2012 | Bar-Or |
| 2012/0094918 A1 | 4/2012 | Bar-Or et al. |
| 2012/0157473 A1 | 6/2012 | Bar-Or |
| 2012/0220530 A1 | 8/2012 | Plumridge et al. |
| 2013/0065839 A1 | 3/2013 | Bar-Or et al. |
| 2013/0072684 A1 | 3/2013 | Bar-Or et al. |
| 2013/0079284 A1 | 3/2013 | Bar-Or et al. |
| 2013/0090292 A1 | 4/2013 | Bar-Or et al. |
| 2013/0303463 A1 | 11/2013 | Bar-Or |
| 2013/0345238 A1 | 12/2013 | Bar-Or et al. |
| 2014/0256642 A1 | 9/2014 | Bar-Or et al. |
| 2014/0286913 A1 | 9/2014 | Bar-Or et al. |
| 2014/0302114 A1 | 10/2014 | Bar-Or |
| 2015/0051223 A1 | 2/2015 | Bar-Or et al. |
| 2015/0051224 A1 | 2/2015 | Bar-Or |
| 2015/0352175 A1 | 12/2015 | Bar-Or et al. |
| 2015/0366932 A1 | 12/2015 | Bar-Or |
| 2016/0015705 A1 | 1/2016 | Bar-Or et al. |
| 2016/0045493 A1 | 2/2016 | Bar-Or |
| 2016/0367644 A1 | 12/2016 | Bar-Or et al. |

FOREIGN PATENT DOCUMENTS

| | | |
|---|---|---|
| CZ | 2827.94 | 4/1996 |
| CZ | 280726 | 4/1996 |
| CZ | 2000-2680 | 7/2000 |
| CZ | 2000-2681 | 7/2000 |
| DE | 4201147 | 7/1993 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | S52-25019 | 2/1977 |
| JP | 59-73574 | 4/1984 |
| JP | 61-112060 | 5/1986 |
| JP | 62-036331 | 2/1987 |
| JP | 63-290868 | 11/1988 |
| JP | 01-013075 | 1/1989 |
| JP | 3176478 | 7/1991 |
| JP | 05-163148 | 6/1993 |
| JP | 07-247474 | 9/1995 |
| JP | 2506541 | 6/1996 |
| JP | 08-277203 | 10/1996 |
| JP | 10-226615 | 8/1998 |
| JP | 10-245315 | 9/1998 |
| JP | 11-504509 | 4/1999 |

(56) References Cited

FOREIGN PATENT DOCUMENTS

| | | |
|---|---|---|
| JP | 2000-327575 | 11/2000 |
| JP | 2001-055340 | 2/2001 |
| JP | 2002-527753 | 8/2002 |
| JP | 2008-505084 | 2/2008 |
| JP | 2009-508658 | 3/2009 |
| JP | 2010-508971 | 3/2010 |
| JP | 2011-507609 | 3/2011 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/14317 | 5/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/057187 | 9/2000 |
| WO | WO 01/34586 | 5/2001 |
| WO | WO 01/64241 | 9/2001 |
| WO | WO 01/91713 | 12/2001 |
| WO | WO 02/011676 | 2/2002 |
| WO | WO 02/012201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/005292 | 1/2004 |
| WO | WO 2004/034060 | 4/2004 |
| WO | WO 2004/048345 | 6/2004 |
| WO | WO 2004/054498 | 7/2004 |
| WO | WO 2004/103304 | 12/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |
| WO | WO 2012/174472 | 12/2012 |

OTHER PUBLICATIONS

Oxford Dictionary, Definition of Antagonist, http://www.oxforddictionaries.com/us/definition/american_english/antagonist, retrieved online on Jun. 15, 2016.*

Suguna et al., "Crystal structures of diketopiperazines containing α-aminoisobutyric acid: Cyclo(Aib-Aib) and cyclo(Aib-L-Ile)," Biopolymers, 1982, vol. 21, Iss. 9, pp. 1847-1855.

Del Fresno et al. "Solid-phase synthesis of diketopiperazines, useful scaffolds for combinatorial chemistry," Tetrahedron Letters, 1998, vol. 39, Iss. 17, pp. 2639-2642.

Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398.

Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398. (Abstract and Graphic only).

Matejschuk et al., "Production of human albumin solution: a continually developing colloid," British Journal of Anaesthesia, 2000, vol. 85, Iss. 6, pp. 887-895.

Pötgens et al., "Covalent dimerization of vascular permeability factor/vascular endothelial growth factor is essential for its biological activity. Evidence from Cys to Ser mutations," The Journal of Biological Chemistry, 1994, vol. 269, Iss. 52, pp. 32879-32885.

Ziong et al., "Chemical Constituents from Phytolacca polyandra" Yunnan Zhiwu Yanjiu, 2002, vol. 24, No. 3, pp. 401-405. (English abstract).

Official Action (English translation) for Chinese Patent Application No. 201280047684.X dated Jul. 15, 2015, 9 pages.

Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.

Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.

Zander et al., "Allogeneic bone marrow transplantation for acute leukemia refractory to induction chemotherapy," Cancer, 1985, vol. 56, Iss. 6, pp. 1374-1379.

"Centricon Centrifugal Filter Devices User Guide," Millipore Corp., Mar. 2005, 23 pages.

Cytokines and Autoimmune Diseases, edited by Kuchroo, et al., 2002, Humana Press Inc., Totowa, NJ, pp. 3-23, 389-406.

Cytokines and Autoimmune Diseases, edited by Kuchroo, et al., 2002, Humana Press Inc., Totowa, NJ, pp. 5, 11, and 391.

Database WPI Section Ch, Week 199844 Derwent Publications Ltd., London, GB; Class B03, AN 1998-515050 XP002369751 & JP 10 226615 A (Pola Chem Ind Inc) Aug. 25, 1998 (Aug. 25, 1998).

"Diabetic Retinopathy—What you should know," National Institutes of Health, 2003, NIH Publication No. 06-2171, 24 pages.

"Disposable PD-10 Desalting Columns," GE Healthcare Life Sciences, downloaded Nov. 1, 2011, 2 pages.

"Desalting and buffer exchange with Sephadex® G-25," Amersham Biosciences, downloaded from www.gelifesciences.com on Jan. 8, 2013, 8 pages.

"Human Albumin," Sigma downloaded from www.sigmaaldrich.com on Jan. 8, 2013, 1 page.

Online Medical Dictionary definition of albumin, medical-dictionary.thefreedictionary.com/albumin, downloaded Nov. 1, 2011, 4 pages.

The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.

The Cytokine Handbook, edited by Thomson and Lotze, 4th edition, 2003 Academic Press, vol. II, London, UK, pp. 838-860 and 1189-1211.

The Cytokine Handbook, edited by Thomson and Lotze, 4th edition, 2003 Academic Press, vol. I, London, UK, pp. 167-199, 456-474, 567-601.

The Dictionary of Immunology, Fourth Edition, Edited by Herbert et al., 1995, pp. 51-52 and 69.

"Tryprostatin A, Aspergillus fumigates," available at www.emdbiosciences.com/Products/ProductDisplay.asp?catno=649305&, printed on Jun. 21, 2006, 1 page.

(56) References Cited

OTHER PUBLICATIONS

't Hart et al., "Evaluating the validity of animal models for research into therapies for immune-based disorders," DDT, 2004, vol. 9(12), pp. 517-524.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Alvarez et al., "Isolation and Structure Elucidation of Two New Calpain Inhibitors from Streptomyces Griseus," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).
Bar-Or et al. "Commercial human albumin preparations for clinical use are immunosuppressive in vitro," Critical Care Medicine, Jun. 2006, vol. 34, No. 6, pp. 1707-1712.
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berman et al., "Psoriasis," PubMed Health, reviewed Nov. 22, 2011, available at www.ncbi.nlm.nih.gov/pubmedhealth/PMH0001470/?report=printable.

Berry et al., "Inhibition of Tau Polymerization by its Carboxy-Terminal Caspase Cleavage Fragment," Biochemistry, 2003, vol. 42, pp. 8325-8331.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.
Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.
Bousquet et al. "Allergic Rhinitis and its Impact on Asthma (ARIA) 2008," Allergy, 2008, vol. 63, Issue Supplement 86, pp. 8-160.
Bousquet et al. "Allergic Rhinitis and Its Impact on Asthma," The Journal of Allergy and Clinical Immunology, 2001, vol. 108, Iss. 5, Supplement, pp. S147-S334.
Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Brauns et al., "Selected cyclic dipeptides inhibit cancer cell growth and induce apoptosis in HT-29 colon cancer cells," Anticancer Research, 2004, vol. 24, pp. 1713-1720.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chan et al., "Site-Specific N-Terminal Auto-Degradation of Human Serum Albumin," Eur. J. Biochem., 1995, vol. 227, pp. 524-528.

(56) References Cited

OTHER PUBLICATIONS

Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of Gymnoascus reessii," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Costa et al., "Aggregation of features of the metabolic syndrome is associated with increased prevalence of chronic complications in Type 2 diabetes," Diabetic Medicine, 2004, vol. 21, Iss. 3, 252-255.
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by Aspergillus fumigatus II. Physico-chemical properties and Structures," The Journal Of Antibiotics, Jun. 1996, pp. 534-540.
D'Alagni et al. "Effect of Urea on the Optical Rotatory Dispersion of Diketopiperazines of I-Serine, I-Alanine, I-Lysine, I-Valine, and I-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Degrassi et al., "Plant Growth-Promoting Pseudomonas putida WCS358 Produces and Secretes Four Cyclic Dipeptides: Cross-Talk with Quorum Sensing Bacterial Sensors," Current Microbiology, 2002, vol. 45, pp. 250-254.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Esposito et al., "The Solution Structure of the C-Terminal Segment of Tau Protein," Journal of Peptide Science, 2000, vol. 6, pp. 550-559.

Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Fdhila et al., "dd-diketopiperazines: antibiotics active against Vibrio anguillarum isolated form marine bacteria associted with cultures of Pecten maximus" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).

(56) References Cited

OTHER PUBLICATIONS

Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.
Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from Pseudomonas aeruginosa and other Gram-negative bacteria," Moleclur Microbiology, 1999, vol. 33(6), pp. 1254-1266.
Hollyfield et al., "Oxidative damage-induced inflammation initiates age-related macular degeneration," Nature Medicine, 2008, vol. 14, No. 2, pp. 194-198.
Hong et al., "Inhibitory effect against Akt of cyclic dipeptides isolated from *Bacillus* sp" J. Microbiol. Biotechnol., 18, 682-685 (2008).
Houston et al., "The cyclic dipeptide CI-4 [cyclo-(I-Arg-d-Pro)] inhibits family 18 chitinases by structural mimicry of a reaction intermediate," Biochem J., Nov. 15, 2002, vol. 368(Pt 1) (Abstract Only Provided).
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.

Ishii, et al. "Incidence of brain tumors in rats fed aspartame," Toxicology Letters, 1981, vol. 7, pp. 433-437.
Iyer et al. "Inflammatory lipid mediators in adipocyte function and obesity." Nature Reviews Endocrinology, Feb. 2010, vol. 6, pp. 71-82.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al. "Asymmetric Reformastky reaction catalyzed by amino acid derivatives," Huaxue Tongbao CKNI, 2001, vol. 10, pp. 637-640 (English Abstract).
Jiang et al., "AKT signaling in regulating angiogenesis," Current Cancer Drug Targets, 2008, vol. 8, pp. 19-26.
Jicha et al., "Sequence Requirements for Formation of Conformational Variants of Tau Similar to Those Found in Alzheimer's Disease," Journal of Neuroscience Research, 1999, vol. 55, pp. 713-723.
Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.
Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).
Kasperska-Zajac et al. "Platelet Activating Factor as a Mediator and Therapeutic Approach in Bronchial Asthma." Inflammation, Apr. 2008, vol. 31, No. 2, pp. 112-120.
Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).
Kilian et al., "Biological activity of selected tyrosine-containing 2,5-diketopiperazines," Pharmazie, Apr. 2005, vol. 60(4), pp. 305-309 (Abstract Only Provided).
Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).
Kobayashi et al., "Neuropeptide Y and histidyl-proline diketopiperazine," Rinsho-Kensa, Japan, Sep. 1987, vol. 21, No. 9, pp. 984-991.
Kopple et al. "Conformation of Cyclo-(I-Threonine)2 and Cyclo-(I-Allo Threonine)2 : A Proton and Carbon N.m.r. Study." International Journal of Peptide Protein Research, Jul. 1981, vol. 18, No. 1, pp. 33-40.
Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).
Kow et al., "The Effects of the TRH Metabolite Cyclo(His-Pro) and Its Analogs on Feeding," Pharmacology, Biochemistry & Behavior, 1991, vol. 38, pp. 359-364.
Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.
Kulikov et al., "Review: The Bioregulatory Role of Platelet-Activating Factor in Intracellular Processes and Cell-Cell Interactions," 1997, www.protein.bio.msu.su/biokhimiya/contents/v63/full/63010057.html, pp. 1-13.
Kullenberg et al., "Intraarticular Corticosteroid Injection: Pain Relief in Osteoarthritis of the Hip?," Journal of Rheumatology, 2004, vol. 31, No. 11, pp. 2265-2268.

(56) References Cited

OTHER PUBLICATIONS

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lee et al., "Characterization of an Elastase Inhibitor Produced by Streptomyces lavendulae SMF11," Journal of Microbiology and Biotechnology, 2000, vol. 10, No. 1, pp. 81-85.

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.

Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug 2000, vol. 294(2) (Abstract Only Provided).

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases," internet document www.ncbi.nlm.nih.gov/sites/entrez, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-13. Epub Aug. 30, 2005, Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).

Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).

Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).

Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).

Morley et al., "Histidyl-proline diketopiperazine decreases food intake in rats," Brain Research, 1981, vol. 210, Iss. 1-2, pp. 475-478.

(56) References Cited

OTHER PUBLICATIONS

Morley et al., "Neuropeptides and appetite: contribution of neuropharmacological modeling," Fed. Proc., Nov. 1984, vol. 43(14), pp. 2903-2907 (Abstract Only Provided).
Moss et al. "Th1/Th2 cells in inflammatory disease states: therapeutic implications," Expert Opinion on Biological Therapy, Dec. 2004, vol. 4, No. 12, pp. 1887-1896.
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Murray et al., "Role of α-Synuclein Carboxy-Terminus on Fibril Formation in Vitro," Biochemistry, 2003, vol. 42, pp. 8530-8540.
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Nitecki et al., "A Simple Route to Sterically Pure Kiketopiperazines" J. Org. Chem., 1968, vol. 33(2), pp. 864-866.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).
Pekary et al., "In vitro Production of a TRH-Homologous Peptide and His-Pro Diketopiperazine by Human Semen," J Androl, 1985, vol. 6(6), pp. 379-385 (Abstract Only Provided).
Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).
Prakash et al., "Synthesis and Biological Activity of Novel Neuroprotective Diketopiperazines," Bioorganic & Medicinal Chemistry, Sep. 2002, vol. 10(9), pp. 3043-3048.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-1587.
Prasad, "Bioactive Cyclic Dipeptides," Peptides, 1995, vol. 16(1), pp. 151-164.
Purves et al. (Eds), Neuroscience, 2001, Sinauer Associates, Inc., 2nd Edition, pp. 75, 367, 400 and 403.
Purves et al., Life: the Science of Biology, 3rd Ed. (1992), p. 376.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.
Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).
Ramírez et al., "Platelet Activating Factor Modulates Microvascular Permeability through Nitric Oxide Synthesis," Microvascular Research, 1995, vol. 50, Iss. 2, pp. 223-234.
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackling the missing elements," Neurol. Sci., Dec. 2005, vol. 26 Suppl. 4, pp. S215-S217.
Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, β, and -γ on Interleukin-8 Gene Expression by Human Gingival Fibroblasts in Culture Upon Stimulation with Lipopolysaccharide from Prevotella Intermedia, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al. "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan 1984, vol. 34(1) (Abstract Only Provided).
Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).
Schlingemann et al., "Role of vascular permeability factor/vascular endothelial growth factor in eye disease," Brit. J. Ophthalmology, vol. 81, 1997, pp. 501-512.

(56) References Cited

OTHER PUBLICATIONS

Sepetov et al., "Rearrangement, Racemization and Decomposition of Peptides in Aqueous Solution," Peptide Research, 1991, vol. 4(5), pp. 308-313 (Abstract Only Provided).
Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).
Shaw et al., "Future of early detection of lung cancer: the role of mouse models." Clin Cancer Res., Jul. 1; 11(13 Pt 2): 4999s-5003s, 2005.
Shimazaki et al., "Diketopiperazine Derivatives, a New Series of Platelet-Activating Factor Inhibitors," Chem. Pharm. Bull., 1987, vol. 35(8), pp. 3527-3530.
Shimazaki et al., "Diketopiperazines as a New Class of Platelet-Activating Factor Inhibitors," J. Med. Chem., 1987, vol. 30, pp. 1706-1709.
Shimazaki et al., "PAF Inhibitory Activity of Diketopiperazines: Structure-Activity Relationships," Lipids, 1991, vol. 26(12), pp. 1175-1178.
Shimi et al., "Isolation of Cairomycins A and C," Antimicrobial Agents and Chemotherapy, Jun. 1981, vol. 19(6), pp. 941-944.
Shukla et al., "Role of Endogenous Cyclo(His-Pro) in Cold-Induced Hypothermia in the Desert Rat (*Mastomys Natalensis*)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).
Skates et al., "Molecular markers for early detection of renal carcinoma: investigative approach," Clin Cancer Res, Sep. 2004, vol. 10(18 Pt 2), pp. 6296S-6301S.
Smith et al., "Lesson 10, vol. 12—Asthma: Evolving Anti-Inflammatory Therapy," www.chestnet.org/education/pccu/vol12/lesson10.html, pp. 1-8, printed Jul. 20, 2000.
Smith et al., "Recent developments in drug therapy for multiple sclerosis," Mult. Scler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Sollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "Lactobacillus plantarum MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suzuki et al., "Effect of cyclic dipeptides containing histidine on pentobarbital narcosis," J. Pharm. Dyn., May 1981, vol. 4(5), pp. 377-379.

Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
Tascioglu et al., "Efficacy of intra-articular sodium hyaluronate in the treatment of knee osteoarthritis," Clinical Rheumatology, 2003, vol. 22, Iss. 2, pp. 112-117.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Varughese et al., "Crystal structure and conformation of cyclo-L-cystine," Int. J. Pept. Protein Res., vol. 18, Jul. 1981, pp. 88-102.
Vogel et al., "Dissiminated tumor cells—Their detection and significance for prognosis of gastrointestinal and pancreatic carcinomas," Virchows Arch, 2001, vol. 439, pp. 109-117.
Walter et al., "Neurohypophyseal hormones, analogs, and fragments: their effect on puromycin-induced amnesia," Proc. Natl. Acad. Sci., Oct. 1975, vol. 72(10), pp. 4180-4184.
Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.
Wang et al., "A facile pathway to synthesize diketopiperazine derivatives," Tetrahedron Lett, 2002, vol. 43, pp. 865-867.
Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).
Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.
Weng et al., "Novel CCK-B receptor agonists: diketopiperazine analogues derived for CCK4 bioactive conformation," Regul Pept, Aug. 1996; vol. 65(1) (Abstract Only Provided).
Wennemers et al., "Diketopiperazine Receptors: A Novel Class of Highly Selective Receptors for Binding Small Peptides," Chem. Eur. J., 2001, vol. 7, No. 15, pp. 3342-3347.
Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.
Wilber et al., "Histidyl-proline diketopiperazine: a potent and chronic appetite-inhibiting neuropeptide," Trans Assoc. Am Physicians, 1986, vol. 99, pp. 245-249.
Wilkes et al. "Patient Survival after Human Albumin Administration: A Meta-Analysis of Randomized, Controlled Trials." Annals of Internal Medicine, Aug. 2001, vol. 135, No. 3, pp. 149-164.
Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).
Woehlecke et al., "Reversal of breast cancer resistance protein-mediated drug resistance by tryprostatin A.," Int J Cancer; Dec. 2003, vol. 107(5) (Abstract Only Provided).
Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).
Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.

(56) References Cited

OTHER PUBLICATIONS

Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al. "Increased hepatic platelet activating factor (PAF) and PAF receptors in carbon tetrachloride induced liver cirrhosis." Gut, Jan. 2004, vol. 53, No. 6, pp. 877-883.
Yi Es, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zeng et al., "Synthesis of a small library of diketopiperazines as potential inhibitors of calpain," Bioorg Med Chem Lett, Jun. 2005, vol. 15(12), pp. 3034-3038.
Zieve, "Multiple sclerosis," PubMed Health, reviewed Sep. 26, 2011, available at www.ncbi.nlm.nih.gov/pubmedhealth/PMH0001747/?report=printable, 10 pages.
International Preliminary Report on Patentability for International (PCT) Patent Application No. PCT/US2012/062152, dated May 8, 2014, 7 pages.
International Search Report prepared by the United States Patent and Trademark Office dated Dec. 13, 2013, for International Application No. PCT/US2012/062152.
Written Opinion prepared by the United States Patent and Trademark Office dated Dec. 13, 2013, for International Application No. PCT/US2012/062152.
Albert, "ABT-491, a highly potent and selective PAF antagonist, inhibits nasal vascular permeability associated with experimental allergic rhinitis in Brown Norway rats" (1997); p. S133, para [0001].
Harada et al., "Essential involvement of interleukin-8 (IL-8) in acute inflammation," Journal of Leukocyte Biology, 1994, vol. 56, Iss. 5, pp. 559-564.
Lupia et al., "Role of tumor necrosis factor-α and platelet-activating factor in neoangiogenesis induced by synovial fluids of patients with rheumatoid arthritis," European Journal of Immunology, 1996, vol. 26, Iss. 8, pp. 1690-1694.
Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Extended European Search Report for European Patent Application No. 12844064.1 dated Feb. 11, 2015, 6 pages.
Official Action for New Zealand Patent Application No. 623879 dated Feb. 12, 2015, 2 pages.
Written Opinion for Singapore Patent Application No. 11201400283R, dated Jan. 30, 2015, 12 pages.
Lindsley et al., "Allosteric Akt (PKB) inhibitors: discovery and SAR of isozyme selective inhibitors," Bioorganic & Medicinal Chemistry Letters, 2005, vol. 15, Iss. 3, pp. 791-764.
Slater, "Gas-liquid chromatography of 2,5-diketopiperazines as their trifluoroacetyl derivatives," Journal of Chromatography A, 1972, vol. 64, Iss. 1, pp. 166-169.
Official Action for Australian Patent Application No. 2012328605 dated Jul. 29, 2016, 3 pages.
Official Action (with English translation) for Japanese Patent Application No. 2014-539051 dated Aug. 16, 2016, 11 pages.
Abu-Zidan et al., "Lexipafant (BB-882): A Potent New Platelet-Activating Factor Receptor Antagonist," Cardiovascular Drug Reviews, 1997, vol. 15, Iss. 3, pp. 232-243.
Sun et al., "Rho and ROCK Signaling in VEGF-Induced Microvascular Endothelial Hyperpermeability," Microcirculation, 2006, vol. 13, Iss. 3, pp. 237-247.
Official Action (English translation) for Chinese Patent Application No. 201280047684.X dated Jan. 4, 2017, 8 pages.
Official Action (English translation) for Chinese Patent Application No. 201280047684.X dated Apr. 12, 2016, 8 pages.
Official Action (with English translation) for Eurasian Patent Application No. 201490737 dated May 19, 2016, 2 pages.
Official Action for European Patent Application No. 12844064.1 dated May 6, 2016, 3 pages.
Official Action for Singapore Patent Application No. 11201400283R, dated Apr. 28, 2016, 13 pages.
Official Action (with English translation) for Eurasian Patent Application No. 201490737 dated Oct. 7, 2015, 7 pages.
Notice of Acceptance for New Zealand Patent Application No. 623879 dated Mar. 16, 2016, 1 page.
Written Opinion for Singapore Patent Application No. 11201400283R, dated Oct. 13, 2015, 11 pages.
He et al., "Evidence for a Role of Platelet-Activating Factor (PAF) in the Pathogenesis of Age-Related Macular Degeneration (AMD)", Investigative Ophthalmology & Visual Science, 2007, vol. 48, Iss. 13, 2 pages. (Abstract only).
Sakkas et al., "T Cells and T-Cell Cytokine Transcripts in the Synovial Membrane in Patients with Osteoarthritis", Clinical and Diagnostic Laboratory Immunology, Jul. 1998, vol. 5, No. 4, pp. 430-437.
Yasukawa, "Inflammation in age-related macular degeneration: pathological or physiological?", Expert Review of Ophthalmology, 2009, vol. 4, Iss. 2, pp. 107-112.
Notice of Acceptance for Australian Patent Application No. 2012328605 dated Jul. 20, 2017, 3 pages.
Official Action (with English translation) for Eurasian Patent Application No. 201490737 dated Apr. 13, 2017, 4 pages.
Official Action for European Patent Application No. 12844064.1 dated Jun. 7, 2017, 3 pages.
Official Action (with English translation) for Japanese Patent Application No. 2014-539051 dated Mar. 28, 2017, 4 pages.
Notice of Allowance (with English translation) for Japanese Patent Application No. 2014-539051 dated Sep. 26, 2017, 2 pages.
Official Action (with English summary) for Mexican Patent Application No. MX/a/2014/003860 dated May 22, 2017, 10 pages.
Official Action (with English translation) for Eurasian Patent Application No. 201490737 dated Dec. 18, 2017, 2 pages.
Official Action for Canadian Patent Application No. 2,846,394 dated Jul. 4, 2018, 4 pages.
Notice of Allowance (with English translation) for Eurasian Patent Application No. 201490737 dated Jul. 25, 2018, 3 pages.
Official Action for Malaysian Patent Application No. PI 2014700473 dated May 15, 2018, 3 pages.
Official Action for Philippines Patent Application No. 1-2014-500715 dated May 8, 2018, 2 pages.

\* cited by examiner

TREATMENT OF RHINITIS

CROSS-REFERENCE TO RELATED APPLICATIONS

This application is a national stage application under 35 U.S.C. 371 and claims the benefit of PCT Application No. PCT/US2012/062152 having an international filing date of Oct. 26, 2012, which designated the United States, which PCT application claimed the benefit of priority under 35 U.S.C. § 119(e) to U.S. Provisional Patent Application No. 61/552,508, filed Oct. 28, 2011 and U.S. Provisional Patent Application No. 61/561,215, filed Nov. 17, 2011, the disclosures of which are incorporated herein by reference.

FIELD OF INVENTION

The invention relates to a method of treating rhinitis. The method comprises administering an effective amount of a pharmaceutical composition comprising a diketopiperazine with amino acid side chains of aspartic acid and alanine (DA-DKP). The invention also provides a pharmaceutical product comprising a DA-DKP containing composition.

BACKGROUND

Rhinitis is caused by chronic or acute inflammation of the mucous membranes of the nose due to viruses, bacteria or irritants. The inflammation results in the generation of excessive amounts of mucous, commonly producing a runny nose, nasal congestion and post-nasal drip. Rhinitis is reported to affect more than 50 million people in the United States alone.

There are several types of rhinitis, including infectious rhinitis, allergic rhinitis and nonallergic rhinitis. Infectious rhinitis is caused by a viral or bacterial infection. Types of infectious rhinitis include the common cold and sinusitis.

Allergic rhinitis affects more than 20% of people worldwide and the prevalence increases annually. Allergic rhinitis causes impaired social life, sleep, school, and work. The quality of life of patients can be altered by the severity and duration of rhinitis. Allergic rhinitis is a proinflammatory immune response to outdoor or indoor allergens, such as dust or pollen. Symptoms can occur year-round or primarily be at certain times of the year, usually in the spring, summer or fall. The Allergic Rhinitis and its Impact on Asthma (ARIA) guidelines outlines the management of allergic rhinitis as allergen avoidance, patient education, pharmacotherapy, and allergen-specific immunotherapy. For pharmacotherapy, ARIA currently recommends intranasal, second-generation H1-antihistamines and an intranasal corticosteroid for moderate to severe persistent disease. See Bousquet et al., *J. Allergy Clin. Immunol.*, 108 (Suppl 5):S147-334 (2001) and Bousquet et al., *Allergy*, 63 (Suppl. 86):8-160 (2008).

Nonallergic rhinitis is rhinitis that is not triggered by allergens or infectious agents. There is still much to be learned about nonallergic rhinitis, but it is thought that the triggers of it cause dilation of the blood vessels in the lining of the nose, which results in swelling and drainage. Types of nonallergic rhinitis include vasomotor, autonomic, hormonal, drug-induced, atrophic and gustatory rhinitis and rhinitis medicamentosa. Triggers of vasomotor rhinitis include smells, fumes, smoke, dust and temperature changes, and vasomotor rhinitis can coexist with allergic rhinitis. Rhinitis medicamentosa is a condition of rebound nasal congestion brought on by extended use of topical decongestants.

SUMMARY OF THE INVENTION

One embodiment of the invention relates to a method of treating rhinitis by administering an effective amount of a pharmaceutical composition comprising a diketopiperazine with amino acid side chains of aspartic acid and alanine (DA-DKP), to an animal in need thereof. In one aspect, the rhinitis is allergic rhinitis.

In one aspect, the effective amount of the DA-DKP in the composition is from about 100 μg to about 3000 μg per day. In another aspect, the effective amount of the DA-DKP in the composition is from about 500 μg to about 1500 μg per day.

In yet other aspects, the administration of the composition comprising DA-DKP, is commenced within 24 hours of diagnosis of rhinitis. In still other aspects, the administration of the composition comprising DA-DKP, is commenced at the appearance of one or more early signs of, or a predisposition to develop, rhinitis. One or more early signs of rhinitis can be rhinorrhea, nasal congestion, nasal itching and sneezing.

In yet other aspects of the method, the DA-DKP is in a composition prepared by removing albumin from a solution of a human serum albumin composition. For example, the step of removing can be by treating the human serum albumin composition by a separation method. Such separation methods can include ultrafiltration, sucrose gradient centrifugation, chromatography, salt precipitation, and sonication. In addition, the step of removing can be by passing the human serum albumin composition over an ultrafiltration membrane with a molecular weight cut off that retains the albumin, and the resulting filtrate contains the DA-DKP. In one aspect, the ultrafiltration membrane has a molecular weight cutoff of less than 50 kDa. In still another aspect, the ultrafiltration membrane has a molecular weight cut off less than 40 kDa, less than 30 kDa, less than 20 kDa, less than 10 kDa, less than 5 kDa or less than 3 kDa.

In yet another aspect, the composition comprising DA-DKP is administered in combination with a second drug suitable for treating rhinitis. For example, the second drug can be selected from antihistamines, decongestants, anti-inflammatories, mast cell stabilizers, leukotriene modifiers and IgE blockers.

Another embodiment of the invention relates to a pharmaceutical product, comprising a DA-DKP containing composition formulated for administration by a route selected from inhalation, insufflation and nasal administration to the nose. In one aspect, the DA-DKP containing composition formulated for administration by inhalation is packaged in a device selected from insufflators, nebulizers, pressurized packs, squeeze bottle, a syringe, a dropper, a spray device, an atomizer device, and an aerosolizer. In one aspect, the pressurized pack can comprise a propellant selected from dichlorodifluoromethane, trichlorofluoromethane, dichlorotetrafluoroethane, and carbon dioxide.

In still another aspect of the pharmaceutical product, the DA-DKP containing composition formulated for administration by inhalation or insufflation comprises a powder mix of the DA-DKP containing composition and a powder base. In one aspect, the powder mix can be in a dosage form selected from capsules, cartridges, gelatin packs and blister packs. The powder mix can be delivered by a device selected from an inhalator, insufflator and metered-dose inhaler.

In yet another aspect of the pharmaceutical product, the DA-DKP containing composition formulated for nasal administration is in a form of drops or sprays. In one aspect, the DA-DKP in the DA-DKP containing composition comprises from about 0.1% (w/v) to about 10% (w/v) of the composition. The drops or sprays can be contained within an intranasal delivery system. In one aspect, the intranasal delivery system comprises an atomizing device. In one aspect, the atomizing device comprises a bottle and pump. In a preferred aspect, the pump is a metered dose pump. The metered dose pump can deliver an intranasal volume of the DA-DKP containing composition. In one aspect, the metered dose pump can deliver an intranasal volume of about 0.15 ml of the DA-DKP containing composition per pump. In still another pharmaceutical product further comprises an aqueous or non-aqueous base comprising one or more agents selected from dispersing agents, solubilizing agents, and suspending agents.

In still another aspect of the pharmaceutical product, the DA-DKP containing composition is formulated for nasal administration in a form selected from ointments, gels and creams. In one aspect, pharmaceutical product further comprises excipients selected from animal fats, vegetable fats, oils, waxes, paraffins, starch, tragacanth, cellulose derivatives, polyethylene glycol, silicones, bentonites, silicic acid, talc, zinc oxide and mixtures thereof. In still another aspect, the pharmaceutical product further comprises an absorption or permeation enhancer. In yet another aspect, the pharmaceutical product further comprises a thickening agent or viscosity enhancer to increase the residence time of the DA-DKP containing composition in the nose. In still another aspect, the pharmaceutical product further comprises a pharmaceutically-acceptable carrier.

In yet other aspects of the pharmaceutical product, the DA-DKP is in a composition prepared by removing albumin from a solution of a human serum albumin composition. For example, the step of removing can be by treating the human serum albumin composition by a separation method. Such separation methods can include ultrafiltration, sucrose gradient centrifugation, chromatography, salt precipitation, and sonication. In addition, the step of removing can be by passing the human serum albumin composition over an ultrafiltration membrane with a molecular weight cut off that retains the albumin, and the resulting filtrate contains the DA-DKP. In one aspect, the ultrafiltration membrane has a molecular weight cutoff of less than 50 kDa. In still another aspect, the ultrafiltration membrane has a molecular weight cut off less than 40 kDa, less than 30 kDa, less than 20 kDa, less than 10 kDa, less than 5 kDa or less than 3 kDa.

DETAILED DESCRIPTION OF THE INVENTION

The invention provides for a method of treating rhinitis, including but not limited to infectious rhinitis, allergic rhinitis and nonallergic rhinitis. The method comprises administering to an animal in need thereof an effective amount of a pharmaceutical composition comprising DA-DKP.

The invention also provides a pharmaceutical product formulated for administration by a route such as inhalation, insufflation or nasal administration to the nose. The composition comprises a DA-DKP containing composition.

Allergic rhinitis is a proinflammatory immune response to outdoor or indoor allergens, such as dust or pollen. Nonallergic rhinitis is rhinitis that is not triggered by allergens or infectious agents. Types of nonallergic rhinitis include but are not limited to vasomotor, autonomic, hormonal, drug-induced, atrophic and gustatory rhinitis and rhinitis medicamentosa.

In order to treat rhinitis, the composition comprising DA-DKP is administered to an animal in need of treatment. Preferably, the animal is a mammal, such as a rabbit, goat, dog, cat, horse or human. Most preferably, the animal is a human.

Effective dosage forms, modes of administration and dosage amounts for the compounds of the invention (i.e., a composition comprising DA-DKP, and preparations comprising a filtrate of DA-DKP, such as a <5000 MW fraction as discussed below) may be determined empirically using the guidance provided herein. It is understood by those skilled in the art that the dosage amount will vary with the particular disease or condition to be treated, the severity of the disease or condition, the route(s) of administration, the duration of the treatment, the identity of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved. Such an acceptable response may be for example when the symptoms of rhinitis are reduced and/or when the symptoms of rhinitis are no longer detected by the subject.

The composition of the present invention may be a pharmaceutical solution having a DA-DKP concentration range with a lower endpoint of about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, about 210 µM, about 220 µM, about 230 µM, about 240 µM, about 240, about 250 µM, about 260 µM, about 270 µM, about 280 µM, about 290 µM, about 300 µM, about 310, about 320 µM, about 330 µM, about 340 µM, about 350 µM, about 360 µM, about 370 µM, about 380 µM, about 390 µM, or about 400 µM. The composition of the present invention may be a pharmaceutical solution having a DA-DKP concentration range with an upper endpoint of about 600 µM, about 580 µM, about 570 µM, about 560 µM, about 550 µM, about 540 µM, about 530 µM, about 520 µM, about 510 µM, about 500 µM, about 490 µM, about 480 µM, about 470 µM, about 460 µM, about 450 µM, about 440 µM, about 430 µM, about 420 µM, about 410 µM, about 400 µM, about 390 µM, about 380 µM, about 370 µM, about 360 µM, about 350, about 340 µM, about 330 µM, about 320 µM, about 310 µM, about 300 µM, about 290 µM, about 280, about 270 µM, about 260 µM, about 250 µM, about 240 µM, about 230 µM, about 220 µM, about 210 µM, or about 200 µM.

An effective amount of DA-DKP in the composition of the present invention for treating rhinitis can be a range with a lower endpoint of about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 425 µg, about 450 µg, about 475 µg or about 500 µg. An effective amount of DA-DKP in the composition of the present invention for treating rhinitis can be a range with upper endpoint of about 500 µg, about 490 µg, about 480 µg, about 470 µg, about 460 µg, about 450 µg, about 440 µg, about 430 µg, about 420 µg, about 410 µg, about 400 µg, about 390 µg, about 380 µg, about 370 µg, about 360 µg, about 350 µg, about 340 µg, about 330 µg, about 320 µg, about 310 µg, about 300 µg, about 290 µg, about 280 µg, about 270 µg, about 260 µg, about 250 µg, about 240 µg, about 230 µg, about 220 µg, about 210 µg, about 200 µg, about 190 µg, about 180 µg, about 170 µg, about 160 µg, about 150 µg, about 140 µg, about 130 µg, about 120 µg, about 110 µg, about 100 µg, about 90 µg, about 80 µg, about 70 µg, about 60 µg, about 50 µg, about 40 µg, about 30 µg, or about 20 µg.

Additionally, when the DA-DKP containing composition is administered as a spray composition or formulation and/or as drop composition or formulation, the effective dosage amounts can be a range with a lower end point of about 0.01% (weight/volume (w/v)), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.10% (w/v), about 0.11% (w/v), about 0.12% (w/v), about 0.13% (w/v), about 0.14% (w/v), about 0.15% (w/v), about 0.16% (w/v), about 0.17% (w/v), about 0.18% (w/v), about 0.19% (w/v), about 0.20% (w/v), about 0.25% (w/v), about 0.30% (w/v), about 0.35% (w/v), about 0.40% (w/v), about 0.45% (w/v), about 0.50% (w/v). Most preferably about 0.1% (w/v). Also, when the DA-DKP containing composition is administered as a spray composition or formulation and/or as drop composition or formulation, the effective dosage amounts can be a range with a upper end point about 10.0% (w/v), about 9.0% (w/v), about 8.0% (w/v), about 7.0% (w/v), about 6.0% (w/v), about 5.0% (w/v), about 4.0% (w/v), about 3.0% (w/v), about 2.0% (w/v), 1.0% (w/v), about 0.95% (w/v), about 0.90% (w/v), about 0.85% (w/v), about 0.80% (w/v), about 0.75% (w/v), about 0.70% (w/v), about 0.65% (w/v), about 0.60% (w/v), or about 0.55% (w/v).

The administration of the DA-DKP containing composition may be commenced within 24 hours of diagnosis of rhinitis. The administration of the DA-DKP containing composition may be commenced at the appearance of one or more early signs of, or a predisposition to develop, rhinitis. The early signs of rhinitis include but are not limited torhinorrhea, nasal congestion, nasal itching and sneezing.

The compounds of the present invention (i.e., a composition comprising DA-DKP, and preparations comprising a filtrate of DA-DKP, such as a <5000 MW fraction as discussed below) may be administered to an animal patient for therapy by any suitable route of administration, including orally, nasally, parenterally (e.g., intravenously, intraperitoneally, subcutaneously or intramuscularly), transdermally, intraocularly and topically (including buccally and sublingually). Preferred is oral, ocular or nasal administration for any disease or condition treatable according to the invention. Especially preferred is nasal administration.

While it is possible for a DA-DKP containing composition of the present invention to be administered alone, it is preferable to administer the DA-DKP containing composition as a pharmaceutical formulation or product. The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the DA-DKP containing compositions of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. Formulations of the present invention may also be administered as bolus, electuary or paste.

In solid dosage forms of the invention for oral administration (capsules, tablets, pills, dragees, powders, granules and the like), the active ingredient (i.e., a composition comprising DA-DKP, and preparations comprising a filtrate of DA-DKP, such as a <5000 MW fraction as discussed below) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical formulations and products include those suitable for administration by inhalation or insufflation or for nasal administration. For administration to the upper (nasal) or lower respiratory tract by inhalation, the DA-DKP containing compositions of the invention are conveniently delivered from a device for inhalation delivery such as an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the DA-DKP containing composition of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For nasal administration, DA-DKP containing compositions of the invention may be administered by means of nose drops or a liquid spray, such as by means of a plastic bottle spray or atomizer or metered-dose inhaler. Liquid sprays are conveniently delivered from pressurized packs.

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Ointments, gels and creams can also be used for nasal administration of the DA-DKP containing compositions of the invention. The active ingredient may be mixed under sterile conditions with a pharmaceutically-acceptable carrier, and with any buffers, or propellants which may be required. The ointments, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Dosage forms for topical administration or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. A drug-impregnated solid carrier (e.g., a dressing) can also be used for topical administration.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents. Also, drug-coated stents may be used.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

While it is possible for a DA-DKP containing composition to be given alone to treat rhinitis, alternatively, the DA-DKP containing composition may be given in combination with one or more other treatments or drugs suitable for treating the rhinitis. For instance, the DA-DKP containing composition can be administered prior to, in conjunction with (including simultaneously with), or after the other treatment or drug. In the case of another drug, the drug and the DA-DKP containing composition may be administered in separate pharmaceutical compositions or as part of the same pharmaceutical composition. Suitable other drugs include antihistamines, decongestants, anti-inflammatories (steroidal and nonsteroidal), mast cell stabilizers, leukotriene modifiers and IgE blockers. Specific suitable drugs include fexofenadine, doxylamine, diphenhydramine, tripolidine, loratidine, cetirizine, pseudophedrine, phenylephrine, aspirin, ibuprofen, naproxen, prednisone, prednisolone, and methylprednisolone. Suitable drugs for inclusion in a nasal spray are steroids (such as fluticasone propionate, mometasone, budesonite, flunisolide, triamcinolone and beclomethasone), antihistamines (such as azelastine), anticholinergics (such as ipratproium) and mast cell stabilizers (such as cromolyn).

Methods of making diketopiperazines, such as DA-DKP, are well known in the art, and these methods may be employed to synthesize the diketopiperazines of the invention. See, e.g., U.S. Pat. Nos. 4,694,081, 5,817,751, 5,990,112, 5,932,579, 6,555,543; US Patent Application Publication Number 2004/0024180, PCT applications WO 96/00391 and WO 97/48685, and Smith et al., Bioorg. Med. Chem. Letters, 8, 2369-2374 (1998), the complete disclosures of which are incorporated herein by reference.

For instance, diketopiperazines, such as DA-DKP, can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determine by the person skilled in the art. It will advantageously be 2-9, preferably 3-7.

When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or tolueneethanol in the presence of acetic acid (e.g., 1%) or triethylamine (e.g., 4%). Typically, basic cyclization conditions are preferred for their faster cyclization times.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made as described below from proteins and peptides. Further, diketopiperazines for use in the practice of the invention can be obtained commercially from, e.g., DMI Synthesis Ltd., Cardiff, UK (custom synthesis).

The DA-DKP composition and/or products of the present invention can be prepared from solutions containing DA-DKP, including from the commercially-available pharmaceutical compositions comprising albumin, such as human serum albumin, by well known methods, such as ultrafiltration, chromatography (size-exclusion chromatography (e.g., Centricon filtration), affinity chromatography (e.g., using a column of beads having attached thereto an antibody or antibodies directed to the desired diketopiperazine(s) or an antibody or antibodies directed to the truncated protein or peptide), anion exchange or cation exchange), sucrose gradient centrifugation, chromatography, salt precipitation, or sonication, that will remove some or all of the albumin in the solution. The resultant DA-DKP-containing composition and/or product can be used and incorporated into pharmaceutical compositions as described above.

Using an ultrafiltration separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDA, less than about 40 kDa, less than about 30 kDa, less than about 20 kDa, less than about 10 kDa, less than about 5 kDa, less than about 3 kDa. Preferably, the filtrate comprises components having molecular weights less than about 5 kDa (also referred to as "<5000 MW"). This <5000 MW fraction or filtrate contains DA-DKP which is formed after the dipeptide aspartate-alanine is cleaved from albumin and subsequently cyclized into the diketopiperazine. The <5000 MW Fraction can be prepared as described in U.S. Pat. No. 7,732,403, the complete disclosure of which is incorporated herein by reference.

Physiologically-acceptable salts of the DA-DKP of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

Kits comprising the pharmaceutical products of the present invention are also provided. The kits can comprise a DA-DKP composition formulated for nasal administration. The DA-DKP can be prepared as described herein, such as by removing albumin from a solution of a human albumin composition. The kits may contain unit-dose or multi-dose sealed containers, for example, squeeze bottles, syringes, a dropper, a spray device, an atomizer device, an aerosolize, a nebulizer, an insufflators or pressurized packs. The kits may be stored in a condition, wherein the contents are ready for direct use. Alternately, the kits may be stored in a lyophilized condition requiring only the addition of the sterile liquid carrier, for example water, immediately prior to use.

As used herein, "a" or "an" means one or more.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein.

Additional objects, advantages and novel features of the present invention will become apparent to those skilled in the art by consideration of the following non-limiting examples. The following experimental results are provided for purposes of illustration and are not intended to limit the scope of the invention.

Example

A Phase Ib randomized, double-blinded, placebo-controlled, parallel group study was performed to evaluate the efficacy of the <5000 MW Fraction for treating allergic rhinitis in adult humans. Briefly, the study was performed as follows.

The subjects were male or female humans, 18-65 years of age, with a history of allergic rhinitis that had been receiving therapy (continuous or intermittent) for more than 1 year. Each subject had a demonstrated sensitivity to at least one seasonal allergen (treegrass pollen) known to induce allergic rhinitis through a standard skin test. Each subject had a minimum subject-reported reflective Total Nasal Symptom Score (rTNSS) of ≥5 on the day of the Screening Visit (day 1).

During a seven-day wash out period (days 1-7), the subjects received no treatment of any type and recorded their symptoms twice a day (in the morning before bathing, consumption of food or beverages or strenuous activities and 12 hours later) using the following scale:

0=absent (no sign/symptom present)
1=mild (sign/symptom clearly present, but minimal awareness; easily tolerated)
2=moderate (definite awareness of sign/symptom that is bothersome but tolerable)
3=severe (sign/symptom that is hard to tolerate; causes interference with activities of daily living and/or sleeping)

The subjects were randomized into treatment groups (<5000 MW Fraction or placebo (i.e. saline)) after the wash out period (on day 8).

Treatment was begun on day 8 and continued through day 17 (10 days total). During treatment, the subjects again recorded their symptoms twice daily (as described above and before administration of the test medications in the morning) using the above scale. The subjects administered 0.3 ml of one of the test medications, 0.15 ml per nostril, once daily in the morning, immediately after recording their symptoms. The first administration of test medications was supervised by test site personnel. The test medications were the <5000 MW Fraction (containing 3.72% DA-DKP) used as a nasal spray and placebo spray (containing normal saline, 0.9% NaCl) in identical intranasal spray format.

Efficacy of the Test Medications was Assessed as Follows:

The measures of effectiveness in this study included the subject-reported Total Nasal Symptom Score (TNSS). The TNSS is defined as the sum of the subject-reported symptom scores for the four nasal symptoms: rhinorrhea (runny nose), nasal congestion, nasal itching, and sneezing. Each score is assessed on a severity scale ranging from 0 to 3 as defined above.

The subjects were asked to assess both reflective TNSS (i.e., an evaluation of symptom severity over the past 12 hours prior to the recording of the score) and instantaneous TNSS (i.e., an evaluation of the symptom severity over the last 10 minutes).

The reflective and instantaneous TNSS are defined as the sum of the subject-reported symptom scores for the four nasal symptoms. Each subject recorded the symptom scores in the subject's diary. For each score, information recorded in the diary included the following:

rhinorrhea (runny nose)
nasal congestion
nasal itching
sneezing

The severity scale for each symptom evaluation is given above.

Mean reflective (r) and instantaneous (i) subject-reported total nasal symptom scores (TNSS) were calculated for each subject. The mean TNSS is the average of all AM and PM daily scores (each score is ranked on a scale from 0-12) during the baseline (baseline efficacy value) and the treatment period (double-blind efficacy value).

The change in efficacy was calculated as the change in the double-blind value—baseline value as follows:

Change in rTNSS: mean double-blind rTNSS—mean baseline rTNSS
Change in iTNSS: mean double-blind iTNSS—mean baseline iTNSS Student's t-test: mean (SD) difference between treatment groups for the following:

Mean change in (rTNSS/iTNSS)
Mean change in AM (rTNSS/iTNSS)
Mean change in PM (rTNSS/iTNSS)
Mean change in individual symptom scores for each of the four nasal symptoms.

The results obtained by analysis using the Student's t-test are provided in Tables 1-5 and are summarized below (number of subjects who completed the trial at the time of the interim analysis: n=20; placebo, n=10 (Intent to Treat (ITT) population; >5000 MW Fraction, n=10 (ITT population).

rTNSS: <5000 MW Fraction showed a 2.4 point decrease in reflective symptom severity compared to 1.7 point decrease with placebo (Table 2). There was 35% improvement in rTNSS with <5000 MW Fraction versus 23% improvement with placebo. The largest improvements were with sneezing and runny nose symptoms (Table 3). 6/7 efficacy measures showed a larger improvement with <5000 MW Fraction than placebo (all assessments but itchy nose symptom). There was significant rTNSS improvement in subset with baseline rTNSS<median (7.5).

TABLE 1

Baseline efficacy variables, mean (SD)

| Efficacy Variable | Placebo | <5000 MW Fraction | T-test p value |
|---|---|---|---|
| rTNSS | 7.46 (1.71) | 6.84 (1.39) | 0.39 |
| iTNSS | 7.40 (1.71) | 6.45 (1.11) | 0.16 |
| PNSS (screening) | 6.50 (1.43) | 5.60 (1.65) | 0.21 |
| PNSS (randomization) | 6.90 (1.60) | 5.50 (0.85) | 0.03 |

PNSS = Physician Nasal Symptoms Score; TNSS = Total Nasal Symptoms Score

TABLE 2

Mean change in rTNSS

| Efficacy Variable | Saline n = 10 Mean (SD) | <5000 MW Fraction n = 10 (SD) | T-test p value |
|---|---|---|---|
| rTNSS | −1.71 (1.82) | −2.37 (2.06) | 0.46 |
| AM rTNSS | −1.68 (1.69) | −2.25 (2.00) | 0.51 |
| PM rTNSS | −1.72 (1.95) | −2.03 (2.08) | 0.74 |

TABLE 3

Mean Change in Reflective Symptoms

| Symptom | Saline n = 10 Mean (SD) | <5000 MW Fraction n = 10 (SD) | T-test p value |
|---|---|---|---|
| rRunny nose | −0.33 (0.8) | −0.60 (0.8) | 0.45 |
| rStuffy nose | −0.58 (0.6) | −0.59 (0.5) | 0.97 |
| rItchy nose | −0.54 (0.6) | −0.53 (0.6) | 0.97 |
| rSneezing | −0.26 (0.3) | −0.65 (0.7) | 0.13 | iTNSS: <5000 MW Fraction showed a 2.0 point decrease in instantaneous symptom severity compared to 1.7 point decrease with placebo (Table 4). 5/7 efficacy measures showed a larger improvement with <5000 MW Fraction than with placebo. The largest improvements were with sneezing nose symptoms (Table 5). Smaller improvements were seen with instantaneous versus reflective symptoms.

TABLE 4

Mean Change in iTNSS

| Efficacy variable | Saline n = 10 Mean (SD) | <5000 MW Fraction n = 10 (SD) | T-test p value |
|---|---|---|---|
| iTNSS | −1.68 (1.84) | −1.97 (2.06) | 0.75 |
| AM iTNSS | −1.55 (1.69) | −1.84 (1.94) | 0.73 |
| PM iTNSS | −1.50 (1.61) | −1.56 (1.98) | 0.94 |

TABLE 5

Mean Change in Instantaneous Symptoms

| Symptom | Placebo Mean (SD) | <5000 MW Fraction (SD) | T-test p value |
|---|---|---|---|
| iRunny nose | −0.27 (0.8) | −0.37 (0.8) | 0.78 |
| iStuffy nose | −0.54 (0.4) | −0.53 (0.6) | 0.98 |
| iItchy nose | −0.63 (0.6) | −0.46 (0.6) | 0.53 |
| iSneezing | −0.24 (0.6) | −0.61 (0.5) | 0.16 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed:

1. A method of reducing the severity of the symptoms of allergic rhinitis comprising administering an effective amount of a pharmaceutical composition comprising a diketopiperazine with amino acid side chains of aspartic acid and alanine (DA-DKP), to an animal in need thereof, wherein the DA-DKP is in a composition prepared by removing albumin from a solution of a human serum albumin composition, wherein the effective amount of the DA-DKP in the composition is about 100 μg to about 3000 μg per day.

2. The method of claim 1, wherein the effective amount of the DA-DKP in the composition is about 500 μg to about 1500 μg per day.

3. The method of claim 1, wherein administration of the composition comprising DA-DKP, is commenced within 24 hours of diagnosis of allergic rhinitis.

4. The method of claim 1, wherein administration of the composition comprising DA-DKP, is commenced at the appearance of one or more early signs of allergic rhinitis.

5. The method of claim 4, wherein the one or more early signs of allergic rhinitis are selected from the group consisting of rhinorrhea, nasal congestion, nasal itching and sneezing.

6. The method of claim 1, wherein the step of removing the albumin comprises treating the human serum albumin composition by a separation method selected from the group consisting of ultrafiltration, sucrose gradient centrifugation, chromatography, salt precipitation, and sonication.

7. The method of claim 6, wherein the step of removing comprises passing the human serum albumin composition over an ultrafiltration membrane with a molecular weight cut off that retains the albumin, and wherein the resulting filtrate comprises DA-DKP.

8. The method of claim 7, wherein the ultrafiltration membrane has molecular weight cutoff of less than 50 kDa, less than 40 kDa, less than 30 kDA, less than 20 kDa, less than 10 kDa, less than 5 kDa or less than 3 kDA.

9. The method of claim 1, wherein the composition comprising DA-DKP is administered in combination with a second drug suitable for treating rhinitis.

10. The method of claim 9, wherein the second drug suitable for treating rhinitis is selected from the group consisting of antihistamines, decongestants, anti-inflammatories, mast cell stabilizers, leukotriene modifiers and IgE blockers.

* * * * *